United States Patent [19]

Sugimoto et al.

[11] 3,961,080

[45] June 1, 1976

[54] PROCESS FOR AUTOLYSIS OF YEAST

[75] Inventors: Hiroshi Sugimoto; Hiroyuki Takeuchi, both of Noda; Tamotsu Yokotsuka, Nagareyama, all of Japan

[73] Assignee: Kikkoman Shoyu Co., Ltd., Noda, Japan

[22] Filed: Oct. 3, 1973

[21] Appl. No.: 403,262

[30] Foreign Application Priority Data

Oct. 17, 1972  Japan.............................. 47-103868

[52] U.S. Cl..................................... 426/60; 195/74
[51] Int. Cl.².................... A23L 1/28; C12C 11/34
[58] Field of Search ................... 426/60, 429, 62, 2, 426/53, 54; 195/74, 82

[56] References Cited
UNITED STATES PATENTS 1,869,721  8/1932  Sure..................................... 424/195

2,141,455  12/1938  Weizmann........................... 426/60
3,862,337  1/1975  Osborne........................... 426/60 X

FOREIGN PATENTS OR APPLICATIONS 596,847  1/1948  United Kingdom
25,101  1898  United Kingdom

*Primary Examiner*—David M. Naff
*Attorney, Agent, or Firm*—Schuyler, Birch, Swindler, McKie & Beckett

[57] ABSTRACT

Yeasts are autolyzed to produce yeast extracts by adding sodium chloride and ethanol to active yeasts so as to make their concentrations 2 to 10 % (W/V) and 1 to 9 % (V/V) of the total volume of the autolytic reaction system respectively and thereafter subjecting said yeasts to autolysis. The thus obtained yeast extracts have a good flavour and palatability.

8 Claims, No Drawings

PROCESS FOR AUTOLYSIS OF YEAST

This invention relates to a process for producing yeast extracts. More particularly, it relates to a process for producing yeast extracts having an improved quality with a high yield by autolysing active yeasts in the presence of sodium chloride and ethanol.

There have been hitherto known various methods as a process for producing yeast extracts. Among them, there is a process for producing yeast extracts by utilizing autolytic activity of yeasts.

So called "autofermentation", that is, autolysis which is based on the activities of various enzymes contained in yeasts with consumption of storage carbohydrates, will occur by merely allowing yeasts to stand at a temperature of 30°C to 70°C. This method, however, needs an extremely long period until autolysis starts. Therefore, there is a lot of risk of deterioration due to contamination with microorganisms in the course of processing. Moreover, since autolysates demonstrate usually a bitter taste, this method cannot be utilized on industrial scale at all.

Thus, there is often utilized, industrially, a process wherein yeasts are compelled to plasmolysis to make them mud-like form with adding as a "trigger-agent" for autolysis, a non-polar organic solvent such as, toluol, chloroform, ethyl acetate or amyl acetate; or an inorganic salt such as sodium chloride or the like in order to shorten the process necessary for starting the autolysis, and the resultant is allowed to stand at a temperature of 30°C to 70°C, thereby autolysis caused by various enzymes contained in yeasts occurs.

In this process, the addition of said organic solvent as a "trigger-agent" for autolysis can prevent practically contamination with microorganisms during autolysis and this leads to prevention of deterioration or putrefaction. However, even as processing means it would be not favorable to utilize such substance which is not approved as a food additive in food processing and it is advisable to avoid utilizing such substance.

On the other hand, there is no problem in adding sodium chloride from food safety viewpoints, but the addition of sodium chloride in a considerable quantity is required in order to obtain a high quality autolysate having no deterioration due to contamination with microorganisms since it is clearly inferior in the effect for prevention of contamination with microorganisms. This, however, results in the delay of autolysis because the activities of various enzymes participating in autolysis are, more or less, inhibited. Therefore, it is difficult to obtain high quality yeast extracts with a high yield. Additionally, since a large part of sodium chloride added thereto is transferred into the final product, yeast extracts, and it increases the content of sodium chloride therein, the occasion that the use of the product is restricted to a certain purpose will occur if the quantity of the salt employed is too much.

For instance, in the case of compressed baker's yeasts, the plasmolysis due to the addition of sodium chloride will induce by adding 1 to 5 g. of sodium chloride to 100 g. of the yeasts. Therefore, there is a case that such condition is employed industrially, but the plasmolysis cannot always proceed completely when used such a concentration of sodium chloride. Thus, the following autolysis cannot proceed smoothly. In addition to this, the protection against contamination with microorganisms during autolysis becomes insufficient. Accordingly, the yield of the yeast extracts obtained by the process is low and the quality thereof is not too excellent.

In order to prevent contamination with microorganisms completely during autolysis, the addition of 12 g or more of sodium chloride to 100 g of pressed bread yeasts is required, but the delay of autolysis due to sodium chloride occurs, as previously stated, in the presence of such a high concentrate sodium chloride. This leads to large drawbacks that a long period is needed in processing, nevertheless, that the yield is low and that the quantity of sodium chloride in the finish product, yeast extracts becomes excess.

The present inventors have conducted a great number of study on a method which can sweep away said drawbacks in the process for producing yeast extracts by plasmolysis or autolysis wherein sodium chloride is employed as a "trigger-agent" for autolysis, that is, a process for producing yeast extracts wherein while keeping the quantity of sodium chloride to be added as low as possible, making plasmolysis, that is to say, complete muddling of yeasts and preventing contamination with microorganisms during the following autolysis, the yeast extracts which have far excellent flavour as compared with those obtained by the conventional processes are obtained in a high yield and in a short time, and have found that the above-mentioned requirements can be fulfilled by adding the definite quantities of both sodium chloride and ethanol to the system of yeast autolytic reaction and have completed the present invention as a result of conducting the study intensively based on said findings.

An object of the present invention is to provide a process for producing yeast extracts in a high yield, which comprises making yeasts autolyse in the presence of sodium chloride and ethanol.

Another onject of the present invention is to provide yeast extracts having an excellent flavour and taste.

Still another object of the present invention can be made clear from the following disclosure.

The process for producing yeast extracts according to the present invention can be conducted by adding both sodium chloride and ethanol to active yeasts at the rate of 2 to 10 weight by volume (W/V) percents and 1 to 9% volume by volume (V/V) percents of the total volume of the autolytic reaction system, respectively, and making said yeasts autolyse.

Hereinafter, the ratio of sodium chloride in the system of autolytic reaction is expressed in weight (g) of sodium chloride in the total volume (100 ml) of said system of the autolytic reaction and it is shown in the term of "% (W/V)" and the ratio of ethanol in said system is expressed in volume (ml) of ethanol in the total volume of said reaction system (100 ml) and it is shown in the term "% (V/V)".

According to the present invention, there is observed an marked increase in yield of pure yeast extracts, as compared with the reference process wherein ethanol is not added. Especially, in the present extracts, the yields of the total nitrogen, formol nitrogen, particularly free glutamic acid and the like increase to a great extent and nitrogen-containing palatable ingredients represented by peptides and amino acids, especially, glutamic acid are formed in a large quantity. In this case, the resultant autolysate shows not any unfavorable taste including bitterness at all, but strong meat extracts-like flavour. That is, there are observed not only an increase in yield of yeast extracts, but also a large effect which improves the quality as a seasoning base for foods simultaneously. The following Experimental Example 1 illustrates one example of the said fact.

Experimental Example 1

To 50 g of commercially available compressed baker's yeasts (Products of Oriental Yeast Industry Co., Ltd.: water content: 69.22%, total nitrogen: 2.65%), were added 3 g of sodium chloride to make yeast mud. Then water was added until the total volume became 60 ml. The resultant was used as a control. On the other hand, a series of mud-like materials having the definite ethanol concentrations shown in Table 1 was prepared by using mixture of ethanol and water instead of water in the control. Those mud-like materials were allowed to stand at 40°C for 72 hours to autolysis. In that case, the sodium chloride concentration of each mud-like material was 5% (W/V).

During autolysis, each mud-like material was stirred occasionally in order to make homogeneous the whole reaction system comprising yeasts, sodium chloride, ethanol and water. Thereafter, water was added to each mud-like material until the total volume become 100 ml. The resultants were subjected to steam-heating treatment at 100°C for 30 minutes in an autoclave to make enzymatic activities inactive. After cooling to a room temperature, insoluble residues were removed by means of centrifugation to obtain the liquid portion. That is, the autolysate liquid was collected. The residues were suspended in 50 ml of hot water and the washing was collected by means of centrifugation. This procedure was repeated twice.

The respective washings were combined with the autolysate liquid and the combined liquid was subjected to concentration under reduced pressure by using a rotary evaporator until the total volume of each combined liquid become 100 ml. As to the resultants, a soluble total nitrogen (determined based on Kjeldahl's method), a quantity of pure extracts [a value obtained by substracting the content of sodium chloride from the quantity of the total extracts (soluble solid)], formol nitrogen and free glutamic acid (determined by enzymatic method) were determined, respectively. The recoveries of the foregoing two quantities and the ratios of formol nitrogen and free glutamic acid to the quantity of pure extracts were calculated. As to formol nitrogen, the crude protein was calculated out by multiplying the found by 6.25. The results obtained are shown in Table 1.

ing the concentration of ethanol in the mud-like material to at least 5 to 7%.

Furthermore, as to the contents of formol nitrogen and free glutamic acid in pure extracts, there was similarly observed an awful increase with increase of the alcohol concentration in the mud-like material. Especially, the latter became the maximum at 9% of alcohol concentration. According to the present process, there was observed a considerable improvement in not only the yield of yeast extracts, but also the quality as a seasoning base for foods.

Particularly, in order to confirm the latter effect, after lyophilizing the analytical sample, the resultants were crushed to powder. Two aqueous solutions containing respectively 2% (W/V) of powdered extracts of the control and Test-5 were prepared. The resultant solutions were subjected to a sensory evaulation test using well-trained 26 panels with employing triangle system. All of them could distinguish the sample of Test-5. In palatability test of 26 persons, 25 persons pointed out that the sample of Test-5 was superior to that of the control.

In the comparison test of the above-mentioned Experimental Example 1, the concentration of sodium chloride in the mud-like material was kept at the definite level (5.0% W/V) and autolysis was carried out in the absence of ethanol. In such a case that ethanol is absent, a favorable result would not be expected even if the concentration of sodium chloride was changed. The following Experimental Example 2 illustrates an example of the aforesaid fact.

Experimental Example 2

To each 50 g of the same compressed baker's yeasts as used in Experimental Example 1, were added 1.2 g and 6 g of sodium chloride, respectively. After the mixture became mud-like, water was added, respectively until the respective total volume became 60 ml. In this case, the concentrations of sodium chloride in the respective mud-like materials were 2% and 10% (W/V), respectively.

Those mud-like materials were subjected to autolysis under a similar condition to that in Experimental Example 1. In the same manner as that in Experimental Example 1, 100 ml of each concentrated liquid under reduced pressure was obtained. However, in a test wherein the concentration of sodium chloride was 2% (W/V), 2 droplets of toluol were in advance added to the mud-like material as an antiseptic in order to prevent deterioration of autolysate due to contamination Table 1

| Test No. | Concentration of EtOH in mud-like material (%, V/V) | Recovery of pure extracts (%) | Recovery of total nitrogen (%) | (Formol nitrogen) × 6.25 pure extracts (%) | Free glutamic acid pure extracts (%) |
| --- | --- | --- | --- | --- | --- |
| Control | 0 | 25.9 | 27.8 | 22.3 | 1.48 |
| Test-1 | 1.0 | 30.6 | 34.8 | 24.4 | 2.24 |
| Test-2 | 2.0 | 35.7 | 46.2 | 28.3 | 3.16 |
| Test-3 | 3.0 | 44.4 | 59.2 | 30.9 | 3.59 |
| Test-4 | 4.0 | 59.1 | 81.9 | 31.6 | 3.81 |
| Test-5 | 5.0 | 69.2 | 92.7 | 30.6 | 4.36 |
| Test-6 | 7.0 | 65.0 | 90.4 | 29.2 | 4.57 |
| Test-7 | 9.0 | 60.7 | 82.4 | 26.1 | 4.61 |

There was observed a marked increase in yield (recovery) of pure extracts and total nitrogen by increaswith microorganisms during autolysis. The concentrated liquids under reduced pressure were subjected to analysis to give results shown in Table 2.

Table 2

| Test No. | Conc. of sodium chloride in mud-like material (%, W/V) | Recovery of pure extracts % | Recovery of pure nitrogen % | Formol nitrogen × 6.25 pure extracts % | Free glutamic acid pure extracts % |
| --- | --- | --- | --- | --- | --- |
| Test-1 | 2.0 | 24.8 | 21.8 | 19.4 | 0.64 |
| Test-2 | 10.0 | 55.3 | 25.4 | 11.7 | 0.69 |

As is clear from this experiment, if the concentrations of sodium chloride in mud-like materials are adjusted to 2% and 10% (W/V), respectively, in the absence of ethanol, all the values except the recovery of pure extracts under the latter condition were inferior to those of the test wherein the concentration of sodium chloride was 5% (W/V), that is, the control in Experimental Example 1. Especially, the content of free glutamic acid in pure extracts showed an extremely low value. In fact, the palatability of the autolysate prepared under such conditions were very weak. Eventually, the present experiment shows that a favorable result in both yield and quality cannot be expected at all by merely varying the concentration of sodium chloride in the absence of ethanol unless both sodium chloride and ethanol are added together as to be done in the present process.

The existing knowledge concerning the influence of ethanol on autolysis of yeasts is restricted to the one obtained by experiments conducted in the presence of high concentration of ethanol. However, there has been no published knowledge concerning the effect of ethanol on yield of yeast extracts. Expecially, there has been not disclosed the fact that the yield and quality of yeast extracts can be improved simultaneously, as can be seen in the present invention, by making sodium chloride and a relatively low concentrate ethanol coexist at the time of autolysis.

The details of the process of the present invention are given in the followings.

Any yeast, which is a main raw material of the present invention, may be employed irrespective of culturing method and species and the mixture of two or more yeasts may be employed. As yeasts employed in the present process, it is required that the activities of intracellular enzymes are active and they are hereinafter referred to as "active yeasts" in the present invention. That is, it is required that at least a part of yeasts is alive or there is observed the residue in the activities of intracellular enzymes in case of dead yeasts. As an example of the latter, dead yeasts obtained by washing living yeasts with an organic solvent such as methanol, ethanol, hexane, acetone or the like or a weak alkaline solution may be employed.

The species of yeasts is not restricted to certain one, however, as yeasts employed in the present process, it is preferred to use Saccharomyces cereuisial such as baker's yeasts, alcohol yeasts, sake yeasts, wine yeasts, brewer's yeasts or the like; yeasts belonging to Saccharomyces carlsbergensis, so called tolura yeasts belonging to Candida utilis or the like. When used these yeasts as a starting material, the product having a high quality can be easily obtained.

However, yeasts given in the following are usually available at a lower price and those can be also preferably employed. Yeasts obtained by culturing a yeast belonging to Candida such as, for example, Candida tropicalis ATCC-7349, Candida lipolytica NRRL-Y-1095 and the like in a medium containing non-carbohydrates such as, for example, n-paraffin, ethanol and the like as a main carbon source; those obtained by culturing a yeast belonging to Saccharomyces disastaticus IFO-1015, Saccharomyces fragilis OUT-7168, Mycotorula japonica OUT-6226, Torulopsis xylinus OUT-6182, Debaryomyces hansenii OUT-6030, Debaryomyces kloeckeri AHU-3932, Pichia scolyti IFO-1113, Candida guilliermondii OUT-6005 and the like in a medium containing as a main nutrient source spent solubles from sulfite pulp industry, or that from various kinds of agricultural and live-stock products processing industries represented by such as, for example, cheese whey, soy bean whey, spent solubles from potato starch industry, spent solubles from agricultural products canning industry or the like.

It is preferred to use the raw material, yeasts, in a state that the water content is as low as possible such as, for example, dry or pressed yeasts since the quantity of the addition of sodium chloride and ethanol can be saved. However, there is no difficulty in using yeasts having a considerable water content such as, for example, so called "yeast cream" or "yeast milk". The quantity of sodium chloride to be added thereto is not based on weight against yeasts but the total volume of the autolytic reaction system. That is, the concentration is important and sodium chloride is added so as to make the concentration thereof 2 to 10% (w/v). In this case, it is preferred to make the concentration of sodium chloride as low as possible in order to keep the concentration of sodium chloride in the yeast extract product low. When the concentration exceeds 10% (w/v), its use and quantity to be used as a seasoning additive for food are restricted to a great extent since the concentration of sodium chloride in the product becomes greatly high.

In a range that the concentration of sodium chloride is 2 to 10% (w/v) in the autolytic reaction system, an autolysate having a high quality can be obtained in a high yield within a relatively short autolytic reaction time since the autolysis can proceed smoothly without being inhibited when the concentration of sodium chloride is low because of the above-mentioned reason, while, in the case that the concentration of sodium chloride is high, the yeast extract product having a similar quality except the concentration of sodium chloride therein can be obtained in a similar yield to that in a lower sodium chloride concentration by exceeding the autolysis time.

Generally speaking, from the standpoints preventing deterioration of quality due to contamination with microorganisms during autolysis, it is required to add a considerable quantity of ethanol when the concentration of sodium chloride is low while it is possible to make the concentration of ethanol low when the concentration of sodium chloride is high. Therefore, the quantity of ethanol can be saved. It may be obtained yeast extracts by adding 5 or more percents (v/v) of ethanol when no sodium chloride is added or less than 2% (w/v) of sodium chloride is added, but the resultant extracts cannot be used practically since the extracts show organoleptically terrible bitter taste.

In addition to those problems, the hardness or easiness of plasmolysis may vary to a great extent, depending upon the kind of raw material, yeasts. In view of these facts, the concentration of sodium chloride in the autolytic reaction mixture should be carefully decided in a range of 2 to 10% (w/v) with a great caution after conducting a preliminary test.

According to the present invention, however, it is not necessary to bring a complete plasmolysis by adding excess amount of sodium chloride since ethanol is used together.

The following Experimental Example 3 is given to illustrate the influence of the concentration of sodium chloride in the system of the autolytic reaction on the yield and quality of the resultant autolysate, that is, yeast extracts, using baker's yeasts with keeping the concentration of ethanol at the definite level (5%, v/v) and the time of the autolysis at the definite level (72 hrs.).

Experimental Example 3

Each mud-like material containing 5% (v/v) of ethanol with a different concentration of sodium chloride was prepared by adding 3 ml of absolute ethanol and 1.2 to 7.2 g of sodium chloride in turn to 50 g of the same commercially available compressed baker's yeasts as that used in Experimental Example 1, adding further 1N-HCl aqueous solution and water and mixing well so as to make its pH and total volume 4.0 and 60 ml, respectively. On the other hand, as a control, an apparently mud-like material was also prepared by adding 3.5 ml of absolute alcohol and no sodium chloride to 50 g of said yeasts, adding further 1N-HCl aqueous solution and water, mixing well so as to adjust its pH to 4.0 and then adding water so as to make the total volume 70 ml since the autolysis, that is, muddling of yeasts did hardly occur when the total volume became 60 ml. The concentration of ethanol in this control mud-like material was 5% (v/v). Those mud-like materials were allowed to stand at 40°C for 72 hours in order to cause the autolysis. The reaction mixtures consisting of yeasts, sodium chloride, ethanol and the like were stirred occasionally during the autolytic reaction. Following that, water was added to each mud-like material so as to make the total volume 100 ml and the resultant mixture was subjected to steam heating treatment in the same manner as that of Experimental Example 1 and then the autolysate liquid was obtained by centrifugation. Each of residues was subjected to hot water extraction twice in the same manner as that of Experimental Example 1 to obtain washings. The washings were combined with said autolysate liquid. Each combined liquid was subjected to evaporation under reduced pressure so as to make the total volume 100 ml. As to each resultant liquid, the composition of ingredients was determined and the recoveries were calculated in the same manner as that in Experimental Example 1. The results obtained are given in Table 3.

Table 3

| Test. No. | Conc. of sodium chloride in mud-like material (%, w/v) | Recovery of pure extracts (%) | Recovery of total nitrogen (%) | (Formol nitrogen) × 6.25 Pure extracts (%) | Free glutamic acid Pure extracts (%) | Degree of bitterness of autolysate* |
| --- | --- | --- | --- | --- | --- | --- |
| Control | 0 | 57.4 | 83.3 | 32.5 | 3.80 | +++ |
| Test-1 | 2 | 59.6 | 84.4 | 31.4 | 4.25 | ± |
| Test-2 | 4 | 61.8 | 86.4 | 31.6 | 4.35 | — |
| Test-3 | 6 | 65.7 | 85.3 | 30.4 | 3.82 | — |
| Test-4 | 8 | 72.3 | 84.8 | 29.4 | 3.63 | — |
| Test-5 | 10 | 71.0 | 82.5 | 27.2 | 3.42 | — |

Note:
*: +++ terribly strong, ± negligible, — none

This experiment was conducted by using baker's yeasts as a starting material with keeping the concentration of ethanol at the definite level (5%, v/v). Under this condition, there was observed no significant difference in the yield and composition of the yeast autolysate by varying the concentration of sodium chloride in the reaction system in a range of 0 to 10% (w/v), and there was not observed such a large influence as Experimental Example 1 wherein the concentration of ethanol were varied. It has been found that the optimum concentrations of sodium chloride in the reaction mixture for the recovery of pure extracts and the recovery of the total nitrogen are 8 to 10% (w/v) and 4 to 6% (w/v), respectively, and that the optimum concentration of sodium chloride therein for the content of free glutamic acid is 2 to 3% (w/v). The content of formol nitrogen in the pure extracts was high when the concentration of sodium chloride was low. That is, it was at the maximum when the concentration of sodium chloride was zero percent. In this case, now even the autolysate showed terribly bitter taste and such a condition could not be considered as a practical one. In short, it has been cleared that the condition, except that of the control, under which not only the recoveries of the pure extracts and the total nitrogen content, but also the contents of formol nitrogen and free glutamic acid in the pure extracts become the maximum, at least so far as the present example is concerned, is in a range of Tests 1 to 5. In other words, it has been cleared that the concentration of sodium chloride in the system of autolytic reaction is in a range of 2 to 10% (w/v). The control test was carried out under the condition that the concentration of ethanol in the mud-like material was 5% (v/v). Under such a state that no sodium chloride is added thereto, there is not obtained any favorable result at all since the yield of the autolysate liquid would be low or the unfavorable bitterness would be given to the autolysate even if the concentration of ethanol would be varied in a range of 1 to 9% (v/v). This fact is illustrated by the following Experimental Example 4.

Experimental Example 4

An apparently mud-like material was prepared by adding 0.7 ml or 6.3 ml of absolute ethanol to 50 g of the same commercially available compressed baker's yeasts as those employed in Experimental Example 1, and adding further water while mixing well so as to make the total volume 70 ml. In this case, the concentrations of ethanol in the mud-like materials were 1% and 9%, (v/v) respectively.

Those mud-like materials were subjected to autolysis under the same condition as that of Experimental Example 1, and in the same manner as that of Experimental Example 1. 100 ml each of the concentrated mixture of the autolysate and washings of the residue under reduced pressure were obtained.

As to each resultant liquid, the composition of ingredients was determined and the recoveries were calculated in the same manner as that of Experimental Example 1.

The results obtained are shown in Table 4. In the experiment under the condition that the concentration of ethanol is 1% (v/v), since the deterioration of the autolysate due to contamination with microorganisms during the autolysis is unavoidable, 2 droplets of toluol were added in advance to mud-like materials as an antiseptic in order to present the deterioration with contamination.

Table 4

| Test. No. | Conc. of ethanol in mud-like material (%, v/v) | Recovery of pure extracts % | Recovery of total nitrogen % | (Formol nitrogen) × 6.25 Pure extracts % | Free glutamic acid Pure extracts % | Degree of bitterness of autolysate* |
|---|---|---|---|---|---|---|
| Test-1 | 1.0 | 23.7 | 20.2 | 24.3 | 0.32 | ± |
| Test-2 | 9.0 | 60.7 | 84.2 | 33.2 | 6.29 | +++ |

Note:
*: +++ terribly strong, ± negligible

According to this experiment, it has been ascertained that the composition of ingredients and the recoveries in the autolysate are affected to a great extent by changing the concentration of ethanol in the mud-like material under such condition that no sodium chloride is added.

That is, in the case that the concentration of ethanol is 1% (v/v), the recoveries of the pure extracts and the total nitrogen are extremely low and the contents of formol nitrogen and free glutamic acid in the pure extracts are very little. Therefore, an autolysate having a very weak palatability is merely obtained in a poor yield. However, those drawbacks can be removed by increasing the quantity of ethanol to be added. When the concentration of ethanol is 9% (v/v), there is obtained an autolysate whose recoveries of the pure extracts and the total nitrogen are nearly equal to those of the present invention, that is, the case when sodium chloride and ethanol are added together; and whose contents of formol nitrogen and free glutamic acid are slightly superior to those according to the present process.

The autolysate shows a similarly terribly strong and unpleasant bitterness to that of the control one in Experimental Example 3, that is, the one obtained in autolysis under the condition that no sodium chloride is added and the concentration of ethanol in the mudlike material is 5% (v/v).

In short, according to this experimental example, it has been found that the autolysates produced by adding merely ethanol without sodium chloride cannot be practically used as seasoning additive since the yield of the autolysates obtained in the case when the concentration of ethanol in the autolytic reaction system is low are poor and the palatability thereof is weak, and the palatability of the autolysates obtained in the case when the concentration of ethanol is 5 to 9% (v/v) shows terribly strong bitterness while the yield thereof and the composition thereof can be improved.

The viscosity of the reaction system becomes low since the autolysis, that is, an apparent muddling of yeast occurs at once when sodium chloride is added to yeasts, and the decrease in the viscosity of the reaction system can be promoted and become violent by adding thereto ethanol whose quantity is equal to 1 to 9% (v/v) of the total volume of the reaction system, thereby the muddling of yeasts can be promoted greatly.

It is required to choose an adequate concentration of ethanol after carrying out a preliminary test since the optimum quantity of ethanol to be added varies to a considerable extent, depending upon the quantity of sodium chloride and the kind of yeasts, but it is better to avoid the addition of a large amount of ethanol from economical viewpoints since there is expected no better effect other than the increase in the content of free glutamic acid in the extracts by adding over 9% (v/v) of ethanol.

The order in the addition of sodium chloride and ethanol hardly influence on their effects. Sodium chloride may be added prior to the addition of ethanol, or vice versa, ethanol may be added prior to the addition of sodium chloride or sodium chloride and ethanol may be added simultaneously.

Following that, the autolysis is made to proceed by allowing the reaction system muddled by adding sodium chloride and ethanol to yeasts to stand at a temperature of 30°C to 70°C for 4 hours or more. During the autolysis, to give the reaction system a mild stirring or shaking occasionally or continuously is effective to promote the autolysis. Since it is desirable to keep the concentration of hydrogen ion in the reaction system at a pH of 3.0 to 8.0, judging from the efficiency of enzymatic reaction participating in the autolysis, it is better to adjust artificially the concentration of hydrogen ion to a pH within the said range by adding an appropriate acid or alkali whenever it deviates from the above-mentioned range.

The termination of the autolysis is conducted by inactivating the whole or a large part of enzymes participating in the autolysis by subjecting the reaction system to heat treatment at a temperature of 80°C or more, but this heat treatment is conducted as the needs of the case demand. The concentration of hydrogen ion of the thus obtained autolysate is properly adjusted to a pH in a range of 4.0 to 7.0 by adding an appropriate acid or alkali as occasion calls, and the resultant mixture can be used an yeast extract product as it is without removing liquid part or after concentrating or drying in the ordinary manner to make it slurry, paste or powder. This kind of the product can be added to the foods in which the clearness is not required such as, for example, soups such as potage and the like, sauces such as babecue sauce and the like, gravy, stew, dry meat, corned beef, hams and sausages, hamburger, meat pie, meat loaf, curry powder, various baby foods, crackers, biscuits, furikake, paste of sea products, miso and the like to give or enhance the palatability of those processed foods. When applied to foods in which the clearness is required such as, for example, soups such as sumashi soup, bouillion, consomme, ramen soup and the like, liquid condiment such as soy sauce, worcester sauce, soup for Japanese noodles, vinegar and the like, it is necessary to collect in advance the liquid portion, that is, the autolysate liquid, by removing the insoluble residues from the autolysate.

For this purpose, the ordinary filtration or centrifugation is employed. The liquid portion kept in the residue which is still insoluble after subjecting to autolysis can be extracted by washing it with warm or cool water once or more.

When the clearness of the autolysate liquid is insufficient, it can be easily cleared by filtering it using a filter aid such as diatomaceous earth.

The concentration of hydrogen ion of the thus obtained autolysate liquid is properly adjusted to a pH in a range of 4.0 to 7.0 by adding an appropriate acid or alkali as occasion calls, and an yeast extract product in a state of paste or powder by concentrating the resultant liquid in the ordinary manner or drying in the ordinary manner after concentrating.

The above-mentioned adjustment of the concentration of hydrogen ion may be carried out in the course of concentration or after concentration. Whenever insoluble materials forms newly or the confusion thereof occurs in the course of concentration, those materials is removed in the ordinary manner with ceasing concentration procedure, thereby a product having a particularly high solubility can be obtained.

In the case that a higher quality product is required, a lighter-colored yeast extract product having a more excellent flavour can be obtained with lossing hardly the ingredients effective to the palatability by purifying the autolysate liquid using active carbon or other non-ionic absorbant before concentrating or concentrating somewhat.

Since the thus obtained yeast extract product is completely water-soluble, it is possible to add to every kind of the above-mentioned foods. Therefore, it has more use as compared with the yeast extract product obtained without removing the insoluble residue from the autolysate.

According to the present process, yeast extracts improved in its yield and its quality simultaneously to a great extent can be prepared by an easy way, and therefore the present process has a great advantage industrially as a process for producing yeast extracts.

Further details of the present process is illustrated by examples.

EXAMPLE 1 to 5kg of a commercially available compressed baker's yeasts (a product of Oriental Yeast Industry Co., Ltd., water content: 69.22%, total nitrogen: 2.64%) were added 300g of sodium chloride and the resultant was mixed well to obtain the mud-like material.

600ml of 50% (v/v) of ethanol were added thereto and the resultant was allowed to stand at a temperature of 40°C to cause autolysis with stirring gently the whole of the above-mentioned reaction system. After 64 hours have passed, water was added thereto so as to make the total volume 10l and the whole of the above-mentioned reaction system was subjected to steam heating treatment at 100°C for 30 minutes by using an autoclave. After cooling a room temperature, 6.4l of a supernatant (the autolysate liquid) were collected by centrifugation. The residues were suspended in 4l of water again, and this suspension was subjected to treatment in autoclave at the same temperature for the same hours as the above-mentioned procedure. After cooling, a supernatant (washing I) is obtained by centrifugation in the same manner as above. The above-mentioned washing procedure was repeated again to obtain a supernatant (washing II). The washing I and washing II were combined with the above-mentioned autolysate liquid and the whole of the combined liquid was subjected to concentration under reduced pressure by using a flash evaporator. When concentrated until the content of the total extracts reached to about 34% (w/v), there was observed the formation of small quantity of turbidity. Then the concentration was stopped, the turbid material was removed by press-filtration with adding diatomaceous earth equal to 0.5% (w/v) of the total volume. The cleared filtrate was subjected to further concentration under reduced pressure to obtain 1,627g of yeast extract product in a state of paste. The composition of the ingredients in the product was determined according to the standard analytical method for soy sauce [Edited by NIPPON SHOYU GIJITSU KAI (the technical association of soy sauce), 2nd edition, 1966]. The recoveries of pure extracts and the total nitrogen from the raw material yeast was calculated to give the results shown in Table 5.

Table 5

| | | |
|---|---|---|
| Content of total extracts (solid material) | (g/100ml) | 75.20 |
| Content of sodium chloride | (g/100ml) | 17.95 |
| Content of total nitrogen (Kjeldahl's method) | (g/100ml) | 6.93 |
| Content of formol nitrogen | (g/100ml) | 2.91 |
| Content of ammonium nitrogen | (g/100ml) | 0.14 |
| Content of free glutamic acid | (g/100ml) | 2.44 |
| Recovery of pure extracts | (%) | 60.01 |
| Recovery of total nitrogen | (%) | 85.42 |

The thus obtained yeast extract product has no unpleasant taste such as bitterness or roughness. Furthermore, a small of yeasts which is often observed in commercially available yeast extracts products is very weak in the case of the present product and it shows a most strong meat extract-like palatability.

EXAMPLE 2

The same procedure was repeated except that after the reaction had been conducted for 64 hours the whole of the reaction system was subjected to spray drying to obtain 1,920g of yeast extract product in a state of powder (water content: 8.26%).

0.03g of the thus obtained powder product of yeast extracts was added to one pack (content: 10.85g) of a commercially available instant miso soup (Type: Aka-misco, a product of Kikkoman Shoyu Co., Ltd.) and then 300 ml of hot water were added to the resultant to prepare the trial miso soup. On the other hand, the reference miso soup to which the present powdery product of yeast extracts was not added was prepared in a similar manner. When a sensory evaluation test by well-trained 26 panels were repeated by using the miso soup containing no present extracts as a reference, the trial miso soup was preferred in both flavour and palatability at 5 percent level of significance, as compared with the reference miso soup.

EXAMPLE 3

A 10% (w/v) aqueous solution of powdered malt extracts (a product of Difco Research Institute) was prepared and was subjected to steam sterilization. To the resultant solution, was inoculated the seed culture of *Saccharomyces carlsbergensis* IFO-0641 (ATCC-9080) which was an yeast for brewing beer. The culturing was conducted under aerobic condition at 30°C for 48 hours. Yeasts were separated from the broth by centrifugation to collect them. The collected yeasts were washed with water to obtain cleaned yeasts. Dry yeasts (water content: 0.88%, total nitrogen: 8.58%) were obtained by subjecting to the cleaned yeasts freezedrying. To 150g of the dry yeasts were added 450ml of water and the resultant was kneaded well to obtain yeast cream. To the yeast cream, were added 15ml of 99.5% (v/v) ethanol and 30g of sodium chloride in turn and the resultant was mixed well. The whole mixture was allowed to stand at 37°C for 96 hours, and water was added to the resultant so as to make the total volume of the reaction system 1l and then the resultant liquid was subjected to steam heating treatment by using an autoclave at 100°C for 40 minutes. After cooling, a supernatant, that is, the autolysate liquid was collected by centrifugation. The composition of the ingredients in the autolysate liquid and the solubility rates of the pure extracts and the total nitrogen were determined according to the above-mentioned analytical method for soy sauce to obtain the results shown in Table 6.

Table 6

| Content of total extracts (solid material) | (g/100ml) | 13.93 |
|---|---|---|
| Content of sodium chloride | (g/100ml) | 3.60 |
| Content of total nitrogen (Kjeldahl's method) | (g/100ml) | 1.129 |
| Content of formol nitrogen | (g/100ml) | 0.517 |
| Content of ammonium nitrogen | (g/100ml) | 0.036 |
| Content of free glutamic acid | (g/100ml) | 0.44 |
| Solubility rate* of pure extracts | (%) | 57.90 |
| Solubility rate* of total nitrogen | (%) | 73.10 |

Note:
*The "solubility rate" referred herein denotes the rate obtained by dividing the total quantity of the pure extracts or the total nitrogen dissolved in the liquid portion which is calculated based on the volume of the liquid portion calculated from the quantity of added sodium chloride and the concentration thereof in the autolysate liquid by the solid material or the total nitrogen in the starting material.

To the resultant autolysate liquid was added sodium chloride so as to make the final concentration of sodium chloride 18% (w/v). To a commercially available soy sauce (a product of Kikkoman Shoyu Co., Ltd.) was added the resultant liquid until its volume become 2% (v/v) of the total volume to obtain a trial soy sauce. When a sensory evaluation by well-trained 26 panels were repeated by using the same commercially available soy sauce as a reference, there was no significant difference in the flavour while the trial soy sauce was preferred at the 1 percent level of significance in the palatability, as compared with the reference.

EXAMPLE 4

To the same medium containing malt extracts as a nutrient source as that in Example 3 was inoculated with the seed culture of *Candida utilis* IFO-0619 (CBS-L-840) strain which was a torula yeast and the culturing was conducted similarly at 30°C for 48 hours under aerobic condition. The wet yeasts were collected from the broth by centrifugation.

When 50g of sodium chloride were added to 1 kg of the wet yeasts, the plasmolysis occurred at once and apparently mud-like materials (water content: 71.48%, total nitrogen: 2.07%) were obtained. After adding 45ml of 99.5% (v/v) ethanol to 500ml of the mud-like materials, the concentration of hydrogen ion of the reaction system was adjusted to pH 4.0 by using a 1N hydrochloric acid and the total volume was made as 630ml by supplying water.

Thereafter, the whole of the reaction system was allowed to stand 40°C with stirring occasionaly. When 48 hours have passed, 370ml of water were added thereto, and the resultant was subjected to steam heating treatment at 100°C for 30 minutes by using an autoclave. After cooling, a supernatant (the autolysate liquid) was collected by centrifugation. The unrecovered autolysate liquid kept in the residues was extracted by washing the residues with 350ml of hot water in the same manner as that in Example 1. This procedure was repeated twice. All of the washings were combined with the supernatant, and the combined liquid was subjected to concentration under reduced pressure by using a rotary evaporator until the total volume became 380ml. 2g of active carbon were added thereto and the resultant mixture was stirred for 10 minutes for decoloring and deodouring. After removing the active carbon by filtration with suction by using a Buchner funnel, the concentration of hydrogen ion of the filtrate was adjusted to pH 5.80 by adding 1N sodium hydroxide aqueous solution thereto. The resultant liquid was subjected to spray drying, thereby to obtain 187.3g of a light-colored powdery yeast extract product having an excellent flavour and a strong palatability. As to this yeast extract product, the determination of the composition of the ingredients and the calculation of the recoveries of the pure extracts and the total nitrogen were conducted in the same manner as hereinbefore set forth to give the results in Table 7.

Table 7

| Water content | (%) | 1.61 |
|---|---|---|
| Content of sodium chloride | (%) | 26.27 |
| Content of total nitrogen (Kjeldahl's method) | (%) | 8.31 |
| Content of formol nitrogen | (%) | 3.50 |
| Content of ammonium nitrogen | (%) | 0.41 |
| Content of free glutamic acid | (%) | 2.27 |
| Recovery of pure extracts | (%) | 54.14 |
| Recovery of total nitrogen | (%) | 71.60 |

EXAMPLE 5

To 5 kg of defatted soy bean meal product through a low temperature extraction system (a product of Fuji Seiyu Co., Ltd.) was added 50l of water and then the concentration of hydrogen ion of the resulting mixture was adjusted to pH 7.2 by adding dropwise 1N sodium hydroxide aqueous solution and the resultant is warmed. When the temperature thereof went up to 50°C, the mixture was kept at the same temperature for one hour with continuous stirring. Thereafter, the mixture was subjected to filtration with suction by using a Büchner funnel to obtain the liquid portion I. 25% of water was added to the filter cake and the resultant was subjected to the same treatment as mentioned above to obtain the liquid portion II. After the liquid portions I and II were combined, a 1N hydrochloric acid aqueous solution was added thereto to adjust pH. When the pH became 4.4, a large amount of protein was precipitated. The protein was removed by filtration with suction to obtain soy bean whey. 5l of cold water was passed through the filter cake, that is, the separated protein, to obtain the washing which was combined with the said soy bean whey. To the thus obtained soy bean whey was added 1N sodium hydroxide aqueous solution to adjust pH to 5.0 and the resultant was warmed. When the temperature thereof went up to 80°C, the whey was kept at the same temperature for 15 minutes. At that time, since there was observed the coagulation of the heat-coagulable protein, the mixture was allowed to stand at a room temperature overnight to settle the protein precipitate down completely. The supernatant was collected by decantation and it was concentrated under reduced pressure by using a flash evaporator until the total volume became one-third of the initial one. The concentrated supernatant was freeze-dried to obtain 1,255g of the dry material.

A 5% (w/v) aqueous solution of the said material was prepared and the solution was subjected to ordinary steam sterilization. To the sterilized solution was inoculated the seed culture of Debaryomyces kloeckeri AHU-3932 strain. The culturing was conducted under aerobic condition at 25°C for 72 hours and the yeasts were collected by centrifugation. The yeasts were washed with cold water and then washed with cold acetone. The thus treated yeasts were air-dried to obtain powdery yeasts (water content: 2.20%, total nitrogen: 5.91%). To 50g of the thus obtained yeasts were added 250ml of water to make an yeast cream. To the yeast cream were added 24g of sodium chloride and 20ml of 99.5% (v/v) ethanol in turn. With mixing well the whole of the resultant, a 1N hydrochloric acid aqueous solution was added dropwise to adjust pH to 4.0. Thereafter, water was added until the total volume became 400ml.

After the whole mixture was allowed to stand at 40°C for 96 hours, a 1N sodium hydroxide aqueous solution was added to adjust pH to 5.8. Thereafter, the supernatant, that is the autolysate liquid, was collected immediately by centrifugation. The residue was suspended in 300ml of water again, and the washing I was obtained by centrifugation. The above-mentioned washing procedure was repeated further to obtain the washing II. The washings I and II were combined with the thus obtained autolysate liquid. After the combined liquid was concentrated under reduced pressure by using a rotary evaporator until the total volume became about 200ml, the concentrated liquid was subjected to freezedrying. The thus obtained dry material was crushed to obtain 54.7g of powdery yeast extracts. The extracts did not contain any unpleasant flavour, such as, bitterness, roughness or the like and show an extremely rich palatability. The composition of the ingredients of the powdery extracts was determined and the recoveries was calculated in the same manner as hereinabove set forth. The results obtained are shown in Table 8.

Table 8

| | | |
|---|---|---|
| Content of water | (%) | 6.91 |
| Content of sodium chloride | (%) | 43.4 |
| Content of total nitrogen (Kjeldahl's method) | (%) | 4.05 |
| Content of formol nitrogen | (%) | 1.43 |
| Content of ammonium nitrogen | (%) | 0.06 |
| Content of free glutamic acid | (%) | 0.94 |
| Recovery of pure extracts | (%) | 55.6 |
| Recovery of total nitrogen | (%) | 74.6 |

What is claimed is:

1. A process for producing a yeast extract food for humans having good flavour, palatability, and no bitterness comprising adding sodium chloride and ethanol to active bakers yeast and subjecting the resultant mixture to autolysis, said sodium chloride and ethanol being added in amounts such that their concentrations become about 2–10% (w/v) and about 1–9% (v/v) of the total volume of the autolytic reaction system, respectively, said active yeast and said concentrations of said sodium chloride and ethanol being selected such that the resultant autolysate is suitable for human consumption, palatable, and has no bitterness.

2. A process for producing a yeast extract food for humans having good flavour, palatability, and no bitterness comprising adding sodium chloride and ethanol to active yeast selected from the group consisting of *Candia utilis, Saccharomyces disastaticus, Saccharomyces fragilis, Mycotorula japonica, Torulopsis xylinus, Debaryomyces hansenii, Debaryomyces kloeckeri, Pichia scolyti* and *Candia guilliermondii* and subjecting the resulting mixture to autolysis, said sodium chloride and ethanol being added in amounts such that the concentrations become about 2–10% (w/v) and about 1–9% (v/v) of the total volume of the autolytic reaction system, respectively, said active yeast and said concentrations of said sodium chloride and ethanol being selected such that the resultant autolysate is suitable for human consumption, palatable, and has no bitterness.

3. A process for producing a yeast extract food for humans having good flavour, palatability, and no bitterness comprising adding sodium chloride and ethanol to active yeast and subjecting the resultant mixture to autolysis, said sodium chloride and ethanol being added in amounts such that their concentrations become about 2–10% (w/v) and about 5–9% (v/v) of the total volume of the autolytic reaction system, respectively, said active yeast and said concentrations of said sodium chloride and ethanol being selected such that the resultant autolysate is suitable for human consumption, palatable, and has no bitterness.

4. A process for producing yeast extracts according to claim 3 wherein said active yeast is a dead yeast having at least some intracellular enzymes capable of autolyzing the yeast.

5. A process for producing yeast extracts according to claim 3 wherein the active yeast is one member selected from the group consisting of saccharomyces cervisiae, saccharomyces carlsbergensis and candia utilis.

6. A process for producing yeast extracts according to claim 3 wherein the active yeast is one member selected from the group consisting of bakers and brewers yeast.

7. A process for producing yeast extracts according to claim 3 wherein the autolysis is carried out for at least four hours at a temperature of 30°C. to 70°C. at a pH of 3.0 to 7.0.

8. A process for producing yeast extracts according to claim 3 wherein said autolysis is conducted at 40°C.

* * * * *